United States Patent [19] [11] 3,943,949
Ashton et al. [45] Mar. 16, 1976

[54] FLAVORED DENTAL ARTICLES

[75] Inventors: William Howard Ashton, Philadelphia, Pa.; Robert Schenke Russell, South River, N.J.

[73] Assignee: Johnson & Johnson, New Brunswick, N.J.

[22] Filed: Nov. 26, 1974

[21] Appl. No.: 527,327

[52] U.S. Cl. ................................. 132/89
[51] Int. Cl.² ................................. A61C 15/00
[58] Field of Search ........ 132/89, 91, 92 A; 128/62; 424/93

[56] References Cited
UNITED STATES PATENTS

| | | | |
|---|---|---|---|
| 174,619 | 3/1876 | Clark, Jr. | 132/89 |
| 2,700,636 | 1/1955 | Ashton | 167/93 |
| 3,699,979 | 10/1972 | Muhler | 132/89 |
| 3,744,499 | 7/1973 | Wells | 132/92 A |
| 3,800,812 | 4/1974 | Jaffe | 132/89 |
| 3,830,246 | 8/1974 | Gillings | 132/89 |
| 3,837,351 | 9/1974 | Thornton | 132/89 |

*Primary Examiner*—G. E. McNeill
*Attorney, Agent, or Firm*—Steven P. Berman

[57] ABSTRACT

A stabilized, flavored dental article for cleaning the interproximal surfaces of the teeth such as dental floss or dental tape comprising filaments with a wax coating containing spray-dried flavor particles.

7 Claims, 2 Drawing Figures

U.S. Patent March 16, 1976 3,943,949
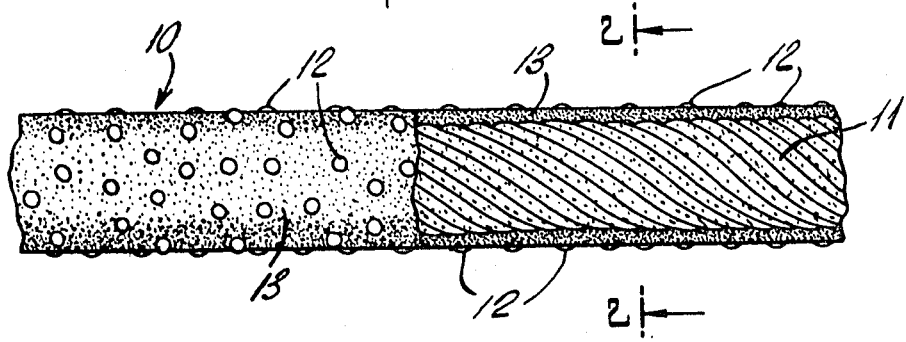
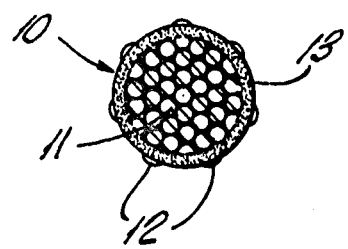

FLAVORED DENTAL ARTICLES

BACKGROUND OF THE INVENTION

This invention relates to articles for cleaning the interproximal surfaces of the teeth and more particularly to flavored dental floss and dental tape.

It has been shown that tooth decay and dental disease can be attributed to bacterial action resulting from the formation of plaque about the teeth and/or the entrapment of food particles between the teeth and interstices therebetween. The removal of plaque and entrapped food particles reduces caries, reduces the tendency towards gingivitis, and reduces mouth odor as well as generally improving oral hygiene. Conventional brushing of the teeth has been found to be unsatisfactory to effect the removal of entrapped food particles from some crevices between the teeth and/or to effectively remove the plaque by which the bacteria adheres to the teeth. To supplement brushing, various materials have been used to clean the interproximal spaces and surfaces of the teeth, for example, dental floss and dental tape. It is to be understood that the use of the term "dental floss" hereinafter encompasses dental tape as well as any similar article.

The use of a flavored dental floss as opposed to the more common unflavored variety provides aesthetic advantages to the floss making the use of said floss more pleasant thereby encouraging better oral hygiene practices.

Prior art dental floss and dental tape products have explored the possibilities of adding various flavors in their production in an attempt to impart a flavor to the finished product. Such products have usually been prepared by the direct addition of flavor oils to the yarn or, in the case of a waxed floss product, the addition of the flavor oils to the wax used to coat the floss. The disadvantage of the direct addition of the flavor oils is that such oils are in most cases volatile and very reactive. As a result of the volatility and reactiveness of these flavor oils, the flavor impression is rapidly lost from the product in a relatively short period of time. Thus, in view of the manufacturing, storage and shelf life times of these products, the consumer will not get the benefits of the addition of the flavors to the product. It has also been suggested to incorporate the flavor oils into a non-wax binder material which is then applied to the floss. It has been found, however, that such a process does not yield a flavored product and it is believed that the flavor is in some manner " locked" into the binder and therefore not released, as desired.

Prior to this invention, it does not appear that any dental floss product was known or available wherein the flavor was stabilized and long-lasting and would not significantly diminish with time and thereby be available when the product was utilized.

SUMMARY OF THE INVENTION

It is an object of this invention to provide improved dental floss and dental tape.

It is a further object of this invention to provide flavored dental floss and dental tape wherein said flavors are stabilized and long-lasting.

It is a still further object of this invention to provide methods of manufacture of dental floss and dental tape with long-lasting, stabilized flavors.

Other objects of this invention will be set forth in, or be apparent from, the following detailed description of the invention.

The foregoing objects and other features and advantages of the present invention are achieved by the use of spray-dried flavor particles to provide a long-lasting, stabilized flavor to dental floss. More specifically, the present invention relates to the use of spray-dried flavor particles wherein flavor oils are dispersed in a matrix of a water-soluble medium to protect the flavor oil from volatilization and oxidation thereby forming a spray-dried flavor particle which is capable of providing a long-lasting, stabilized flavor to dental floss. When an individual utilizes the dental floss and the spray-dried flavor particle contacts an aqueous medium, such as saliva, the water-soluble matrix dissolves thereby releasing the desired flavor.

DESCRIPTION OF THE DRAWINGS

FIG. 1 is a side view partially in section of a part of the flavored dental floss of the present invention.

FIG. 2 is a cross-sectional view taken along line 2—2 of FIG. 1.

DESCRIPTION OF PREFERRED EMBODIMENTS

FIG. 1 illustrates a preferred embodiment of the present invention comprising a flavored dental floss 10 formed of a plurality of individual filaments 11 of a substrate material suitable for use as a dental floss. Such substrate materials include high and normal tenacity nylon such as nylon 6 and 66, rayon, Dacron, acetate polymers, polypropylene and the like as well as cotton, wool and other staple fibers. The plurality of individual filaments are formed together to give a larger thread of a sufficiently small diameter to permit insertion in the interproximal areas between the teeth. If desired, the filaments of yarn can be colored utilizing any compatible and accepted color dye such as FD&C Blue No. 1, FD&C Yellow No. 5, FD&C Red No. 40 and the like.

It is preferred to twist the individual filaments 11 to form the floss 10 in order to give the product additional integrity, that is, additional strength to prevent shredding and filament separation. Dental floss can be made without twisting the individual filaments and dental tape is usually made with little or no filament twist. The twist of the filaments can be from about 1.0 to 3.0 turns per inch, with a preferred twist of about 1.5 to 2.0 turns per inch.

The tensile strength of the finished flavored dental floss should be from about 5 to 25 lbs., although higher tensile strengths are acceptable. The tensile strength of the floss is preferably from about 7 to 15 lbs. If a dental floss with a tensile strength of less than about 5 lbs. is prepared, it will break easily and not be satisfactory for use as a floss. Dental floss with tensile strengths greater than 25 lbs. are satisfactory but offer few additional advantages and are less economical to produce. The thickness of the dental floss should be from about 300 to 2,000 denier, preferably from about 500 to 1,500 denier in order to achieve a satisfactory product.

The spray-dried flavor particles 12 are contained on the surface of or partially embedded in a water-insoluble wax 13. The water-insoluble wax is uniformly distributed on the surface of as well as throughout the filaments forming the floss. The spray-dried flavor particles consist of the flavor oil dispersed in a water-soluble matrix material. Suitable water-soluble materials include gums such as gum acacia, gum arabic, gum tragacanth and the like; starches such as corn starch; dextrins and the like. Suitable materials for use as flavors are those which allow the user to detect a strong, noticeable flavor while permitting the maintenance of an acceptable product appearance. Such flavors include peppermint, spearmint, wintergreen, cassia, cinnamon and the like; fruit flavors such as cherry, strawberry, lime; and the like. Preferred flavors for use in dental floss include peppermint and cassia.

The spray-dried flavor particles can be readily prepared by known spray drying procedures. For example, a suitable flavor oil can be mixed with a solution of a water-soluble matrix material and the resulting mixture is then emulsified by mechanical or other means to form an emulsion. The emulsion thus formed is then passed through suitable spray-drying apparatus to flash off the water present in the emulsion resulting in the formation of a spray-dried flavor particle. The spray-dried flavor particles should be of a particle size of from about $44\mu$ to $840\mu$ with particles of $177\mu$ or smaller being preferred. As discussed above, the spray-dried flavor particles consist of a flavor dispersed in the matrix of a water-soluble medium. The flavor comprises from about 15 to 25% by weight of the spray-dried flavor particle and the water-soluble medium comprises from about 85–75% by weight of the spray-dried flavor particle. The spray-dried flavor particle comprises from about 1 to 10% by weight of the flavored dental floss product.

The stabilized, flavored dental floss of the present invention can be prepared by a number of different methods. Certain of these methods are similar in that the spray-dried flavor particles are attached or affixed to the dental floss after the floss has been passed through a wax bath and the wax is still warm and therefore provides a soft, tacky surface for the spray-dried flavor particles.

The waxes that are preferred are those that are white or colorless and have a melting point of from about 140°F to 200°F. Suitable waxes include beeswax, paraffin and microcrystalline waxes, polyethylene glycols such as those sold under the trademark "Carbowax" by Union Carbide Corp., New York, New York, wax-like resins and polymers and the like as well as mixtures thereof. The wax comprises about 19 to 25% by weight of the dental floss, preferably about 21 to 23% by weight. If less than about 19% by weight of the wax is utilized, there may not be a sufficient amount present to allow the spray-dried flavor particles to sufficiently adhere and if greater than about 25% by weight is present, the finished product may have an unsightly appearance and flaking can occur.

The floss is passed through a wax bath, e.g. by means of directed guides, and while the wax is still semisolid and kept tacky by maintaining the temperature above the setting temperature of the wax, the spray-dried flavor particles are sifted or dusted on the waxed yarn. The sifting or dusting is controlled to give the desired flavor concentration. The temperature is then lowered, e.g. by means of a refrigerated chamber, below the setting temperature of the wax which sets the wax on the filaments and the spray-dried flavor particles are distributed thereon.

Another method of achieving the flavored dental floss comprises drawing the waxed yarn maintained at a high enough temperature to keep it soft and tacky through a pile of sifted spray-dried flavor particles permitting the spray-dried flavor particles to adhere to the wax. When cooling occurs, the wax hardens and the desired flavored floss product results. FIG. 2 shows a cross-sectional view of the resulting product with the individual filaments 11, the water-insoluble wax 13 and the spray-dried flavor particles 12.

Still another method of adding the spray-dried flavor particles comprises spraying the flavor particles onto the waxed floss as the floss is wound on a rewind supply roll immediately after the waxing has occurred. This may also cause some of the spray-dried flavor particles to become partially impregnated in the wax and/or filaments of the floss due to the mechanical compression.

An entirely different method of preparing the flavored dental floss of the present invention involves adding the spray-dried flavor particles directly into the wax bath containing the molten wax. The spray-dried flavor particles are mixed with the molten wax to form a dispersion containing the spray-dried flavor particles dispersed in the wax. The dispersion is continuously mixed to keep it homogeneous and is provided with sufficient heat to keep it in the molten state. The floss is then passed through the wax bath, e.g. by means of directed guides, and an excess of wax containing the spray-dried flavor particles is picked up by the yarn. The waxed yarn can then pass through various mechanical means to remove any excess wax and then the temperature is lowered, e.g. by means of a refrigerated chamber, below the setting temperature of the wax thereby setting the wax containing the spray-dried flavor particles resulting in the finished flavored dental floss.

When samples were prepared in accordance with the present invention and aged at temperatures of from 70°F to 120°F for periods of up to one year, no significant loss of flavor or other negative features such as unsightly discoloring were observed. Thus, the flavored dental floss products prepared in accordance with the present invention are flavor stabilized.

A dental floss or dental tape as described herein exhibits a desirable smooth surface and provides excellent cleaning to the interproximal surfaces of the teeth with a desirable flavor being imparted to the teeth and mouth of the user thereof.

In addition to the preferred embodiments described herein, other arrangements and variations within the spirit of the invention and the scope of the appended claims will occur to those skilled in the art.

What is claimed is:

1. A stabilized flavored article for cleaning the teeth comprising a plurality of filaments of a substrate material formed into a larger thread of a sufficiently small diameter to permit insertion between the teeth, said thread impregnated with water-insoluble wax with spray-dried flavor particles adhered to said water-insoluble wax.

2. The stabilized flavored article of claim 1 wherein the spray-dried flavor particles consist essentially of a flavor oil dispersed in a matrix of a water-soluble medium selected from the group consisting of gums, starches and dextrins.

3. The stabilized flavored article of claim 2 wherein the spray-dried flavor particles comprise about 1 to 10% by weight of the stabilized flavored article.

4. The stabilized flavored article of claim 1 wherein the plurality of filaments are colored with a suitable color dye.

5. The stabilized flavored article of claim 1 wherein the article is dental floss.

6. The stabilized flavored article of claim 1 wherein the article is dental tape.

7. A stabilized flavor article for cleaning the teeth comprising a plurality of filaments of a substrate material formed into a larger thread of a sufficiently small diameter to permit insertion between the teeth; said thread impregnated with a water-insoluble wax with spray-dried flavor particles adhered to said water-insoluble wax consisting essentially of a flavor oil dispersed in a matrix of a water-soluble medium selected from the group consisting of gums, starches and dextrins, with the water-soluble medium being capable of being dissolved by the saliva in the oral cavity when the article is applied to the teeth thereby releasing the flavor to the teeth and oral cavity.

* * * * *